United States Patent [19]

Tubota et al.

[11] Patent Number: 4,933,494
[45] Date of Patent: Jun. 12, 1990

[54] PROCESS FOR PURIFICATION OF DIHYDROXYDIPHENYLSULFONE

[75] Inventors: Hiroyuki Tubota; Hiroshi Kushima; Kazuhiko Sakai; Naoki Yamamoto, all of Fukui, Japan

[73] Assignee: Nicca Chemical Co., Ltd., Fukui, Japan

[21] Appl. No.: 297,077

[22] Filed: Jan. 13, 1989

[30] Foreign Application Priority Data

Jan. 26, 1988 [JP] Japan .................. 63-13573

[51] Int. Cl.$^5$ .................................... C07C 147/10
[52] U.S. Cl. .................................................. 568/33
[58] Field of Search .................... 568/33; 502/414, 415

[56] References Cited

U.S. PATENT DOCUMENTS

| 4,458,030 | 7/1984 | Manabe et al. | 502/414 |
| 4,656,156 | 4/1987 | Misra | 502/414 |

FOREIGN PATENT DOCUMENTS

| 839309 | 4/1970 | Canada . | |
| 0220855 | 5/1987 | European Pat. Off. . | |
| 38-5274 | 5/1963 | Japan . | |
| 42-3005 | 2/1967 | Japan . | |
| 47-20223 | 6/1972 | Japan . | |
| 55-37550 | 9/1980 | Japan . | |
| 57-077664 | 5/1982 | Japan | 568/33 |
| 58-29946 | 6/1983 | Japan . | |
| 58-42186 | 9/1983 | Japan . | |
| 61-024559 | 2/1986 | Japan | 568/33 |
| 62-93271 | 4/1987 | Japan . | |
| 2088857 | 6/1982 | United Kingdom . | |

*Primary Examiner*—Mary E. Ceperley
*Attorney, Agent, or Firm*—McAulay Fisher Nissen & Goldberg

[57] ABSTRACT

Colored dihydroxydiphenylsulfone obtained by a reaction between phenol and sulfuric acid is treated with activated carbon and a hydrotalcite compound in a mixed solvent comprising methanol and water at a weight ratio of from 10/90 to 60/40. According to this process, colored dihydroxydiphenylsulfone can be industrially advantageously purified at a high efficiency.

7 Claims, No Drawings

PROCESS FOR PURIFICATION OF DIHYDROXYDIPHENYLSULFONE

BACKGROUND OF THE INVENTION

(1) Field of the Invention

The present invention relates to a process for the purification of dihydroxydiphenylsulfone. More particularly, the present invention relates to a purification process in which colorless dihydroxydiphenylsulfone is obtained from colored dihydroxydiphenylsulfone obtained by a reaction of phenol with sulfuric acid.

(2) Description of the Related Art

Dihydroxydiphenylsulfone has long been used as an additive to a plating solution, a leather tanning agent, a dyeing assistant, a curing promoter for a phenolic resin, a starting material for a flame retardant, an agricultural chemical and the like. Recently, however, dihydroxydiphenylsulfone has been used as a starting material for engineering plastics such as a polycarbonate, a polyester, and a polyether-sulfone, a starting material for a color photography element and a photographic contrast increaser, a color developer for a pressure-sensitive recording paper, and an additive to a vesicular recording material. In these applications, coloration of the dihydroxydiphenylsulfone must be reduced to a very low level, and the dihydroxydiphenylsulfone heretofore regarded as a purified product fails to satisfy this requirement.

Various processes have been proposed for obtaining dihydroxydiphenylsulfone having a reduced coloration. For example, a process comprising a treatment with a decoloring carbon is disclosed in Japanese Examined Patent Publication No. 38-5274, but a solution of a product treated by this process still has a light pink color. Japanese Examined Patent Publication No. 42-3005 discloses a process in which colored impurities are extracted and removed from a hot aqueous solution maintained at a temperature higher than 120° C. by using an aliphatic higher alcohol. But, separation into an aqueous phase and an alcohol phase at a temperature higher than 120° C. is not advantageous when carried out on an industrial scale. Furthermore, Japanese Examined Patent Publication No. 47-20223 discloses a process in which stoichiometric amounts of phenol and sulfuric acid are reacted at 130° C. to 170° C., benzene is added to the reaction mixture, and water formed by the reaction is removed by azeotropic distillation. Nevertheless, the dihydroxydiphenylsulfone is still colored brown and the hue to the product is not completely satisfactory. Japanese Examined Patent Publication No. 55-37550 discloses a process in which a reaction product is dissolved in an aqueous solution of phenol to separate the solution into two layers, and the lower layer containing oily impurities causing coloration is removed. In this process, an incorporation of phenol into the upper layer containing the purified product cannot be avoided, and this phenol becomes a new cause of coloration. Still further, Japanese Examined Patent Publication No. 58-29946 discloses a process in which dihydroxydiphenylsulfone containing a coloring substance is dissolved in a solvent and a reducing agent is added to the solution to effect decoloring, and Japanese Examined Patent Publication No. 58-42186 discloses a process in which a reaction product is dissolved in an aqueous solution of an alkali and the solution is treated with an inorganic peroxide. These processes, however, cannot produce a purified product having a satisfactory hue, and since the coloring impurity is merely rendered colorless by reduction or oxidation, the product is sometimes recolored if the product is used for a long time or under severe conditions.

In Japanese Unexamined Patent Publication No. 61-24559, the present inventors proposed a purification process comprising two steps of recrystallizing colored dihydroxydiphenylsulfone obtained by a reaction between phenol and sulfuric acid, from a methanol/water mixed solvent having a specific composition, and treating the recrystallization product with an activated carbon having a specific average pore diameter. In this process, however, two steps are necessary for removing coloring impurities. Japanese Unexamined Patent Publication No. 62-93271 discloses a process in which a basic aqueous solution of dihydroxydiphenylsulfone is brought into contact with an activated carbon, the activated carbon is removed by filtration or the like, and an acid is added to the residue to precipitate dihydroxydiphenylsulfone. In this process, however, a base and an acid must be used in amounts substantially equimolar to the dihydroxydiphenylsulfone, and therefore, they form salts and cannot be utilized again. Therefore, the process is not advantageous from the economical viewpoint.

SUMMARY OF THE INVENTION

The present inventors carried out research into ways of overcoming the above-mentioned defects of the conventional techniques and providing a purification process for obtaining a colorless dihydroxydiphenylsulfone, and as a result, it was found that coloring impurities can be removed from colored dihydroxydiphenylsulfone obtained by a reaction between phenol and sulfuric acid by one step of treating the colored dihydroxydiphenylsulfone with activated carbon and a hydrotalcite compound in a methanol/water mixed solvent having a specific composition. The present invention was completed based on this finding.

More specifically, the present invention provides a process for the purification of dihydroxydiphenylsulfone, which comprises heating and mixing colored dihydroxydiphenylsulfone obtained by a reaction between phenol and sulfuric acid with activated carbon and a hydrotalcite compound in a mixed solvent comprising methanol and water at a mixing weight ratio of from 10/90 to 60/40, removing the activated carbon and hydrotalcite compound by filtration, cooling the filtrate, and separating the precipitated crystals.

DESCRIPTION OF THE PREFERRED EMBODIMENTS

The colored dihydroxydiphenylsulfone used in the present invention is obtained by reacting phenol with sulfuric acid. For example, phenol is charged in a reaction tank, sulfuric acid is added in an equivalent amount, the mixture is heated while stirring, and a reaction is carried out while removing water formed by the reaction by distillation. In this reaction, a small amount of phenol is removed by azeotropic distillation. Accordingly, phenol is pre-charged in a slightly excessive amount, or the phenol phase is separated from the distilled aqueous phase and is returned to the reaction tank. Furthermore, a method can be adopted in which phenol is newly added in an amount corresponding to the distilled amount. To promote the reaction, an organic solvent capable of azeotropic distillation with water, such as o-chlorobenzene, can be added. If the pressure of the reaction system is slightly reduced, the distillation of water can be expedited. After termination of the reaction, the reaction mixture is taken out from the reaction tank while still hot, and is cooled to obtain dihydroxydiphenylsulfone in the form of a reddish brown lump.

The colored dihydroxydiphenylsulfone is dissolved by heating in a methanol/water mixed solvent, and is then decolored by activated carbon. The composition of the methanol/water mixed solvent used in the present invention is such that the methanol/water weight ratio is from 10/90 to 60/40, preferably from 20/80 to 40/60. Japanese Unexamined Patent Publication No. 62-93271, teaches that, where colored dihydroxydiphenylsulfone is merely recrystallized from a methanol/water mixed solvent, the composition of the mixed solvent is such that the methanol/water weight ratio is from 40/60 to 95/5, preferably from 50/50 to 90/10, especially preferably from 60/40 to 85/15. But, where a treatment with activated carbon is carried out in a methanol/water mixed solvent, the proportion of methanol in the mixed solvent must be smaller than in the case of mere recrystallization, and if the methanol/water weight ratio is higher than 60/40, not all of the coloring substances are removed. If the methanol/water weight ratio is lower than 10/90, only a small amount of dihydroxydiphenylsulfone is dissolved by heating under an atmospheric pressure, and thus good results cannot be obtained.

The average diameter of pores in the activated carbon used in the present invention is 15 to 60 Å, preferably 20 to 50 Å. If the average pore diameter is smaller than 15 Å or larger than 60 Å, all of the coloring substances cannot be removed. The amount of activated carbon used is not particularly critical, but preferably is 0.5 to 5 parts per 100 parts of colored dihydroxydiphenylsulfone.

The hydrotalcite compound used in the present invention is a hydrate of a composite salt of magnesium carbonate, magnesium hydroxide and aluminum hydroxide, represented by the chemical formula of $Mg_6Al_2(OH)_{16}CO_3.4H_2O$. The hydrotalcite compound includes not only a natural product but also a synthetic product. The composition of the natural product differs to some extent according to the place of production, and the composition of the synthetic compound differs to some extent according to the preparation process, but nevertheless any product can be used in the present invention. Preferably the hydrotalcite compound is used in an amount of 0.1 to 2 parts by weight per 100 parts by weight of the colored dihydroxydiphenylsulfone.

Either a method in which the colored dihydroxydiphenylsulfone is homogeneously dissolved in the methanol/water mixed solvent and the activated carbon and hydrotalcite are added to the solution, or a method in which methanol, water, the colored dihydroxydiphenylsulfone, the activated carbon and the hydrotalcite compound are charged in a dissolving tank and the entire mixture is heated and stirred can be adopted, when removing the activated carbon and hydrotalcite compound by filtration, preferably a filter aid such as diatomaceous earth is used.

When the filtrate remaining after the removal of the activated carbon and hydrotalcite compound is cooled, dihydroxydiphenylsulfone, from which the coloring components have been removed, is precipitated in the form of a crystal. This dihydroxydiphenylsulfone is recovered by filtration and then dried, whereby a purified product having a good hue is obtained. Since dihydroxydiphenylsulfone is still contained in the filtrate remaining after the recovery of the crystal by filtration, all or a part of the filtrate can be used as the solvent at the subsequent decoloring treatment with the activated carbon and hydrotalcite compound.

The present invention will now be described in detail with reference to the following examples, that by no means limit the scope of the invention.

Note, in the examples, the absorbance and Hazen color number were determined by the following methods.

(1) Absorbance

A 20% solution of dihyiroxydiphenylsulfone in methanol was prepared and the absorbance at 420 nm was measured in a cell having an optical path of 10 mm, by a digital double beam spectrophotometer (Model UV-150-02 supplied by Shimazu Seisakusho).

(2) Hazen Color Number

A 20% solution of dihydroxydiphenylsulfone in methanol was prepared and the Hazen color number was determined by comparing the solution with standard solutions shown in JIS K-4101.

EXAMPLE 1

A glass reactor having a capacity of 5 was charged with 1900 g of phenol and 1000 g of 98% sulfuric acid, and a reaction was carried out at 160° C. for 3 hours, at 170° C. for 2 hours, and at 180° C. for 2 hours, while removing water formed by the reaction by distillation. The reaction mixture was taken out and allowed to cool, to obtain dihydroxydiphenylsulfone in the form of a reddish brown lump (hereinafter referred to as "crude dihydroxydiphenylsulfone"). The absorbance of this crude dihydroxydiphenylsulfone was 1.088.

A flask having a capacity of 2 was charged with 258 g of methanol and 602 g of water, and 700 g of the above-mentioned crude dihydroxydiphenylsulfone was added to this mixed solvent (the methanol/water weight ratio was 30/70) and the mixture heated and refluxed, whereby a homogeneous brown solution was formed. Then, 14 g of activated carbon having an average pore diameter of 39 Å and 7 g of synthetic hydrotalcite were added to the so-formed solution, the mixture was heated and refluxed for 1 hour while stirring, and the activated carbon and hydrotalcite were removed by filtration. When the filtrate had cooled to room temperature, a crystal was precipitated. The crystal was separated from the mother liquid by filtration, and when the crystal was dried, 550 g of dihdroxydiphenylsulfone having an absorbance of 0.008 and a Hazen color number of 5 was obtained.

COMPARATIVE EXAMPLE 1

To a mixed solvent comprising 490 g of methanol and 210 g of water (the methanol/water weight ratio was 70/30) was added 900 g of crude dihydroxydiphenylsulfone synthesized in the same manner as described in Example 1, and the mixture was heated and refluxed to obtain a homogeneous brown solution. Then, 18 g of the same activated carbon as used in Example 1 and 9 g of synthetic hydrotalcite were added to the so-formed solution. The mixture was heated and fluxed while stirring for 1 hour, and the activated carbon was removed by filtration to obtain a light-brown filtrate. when the filtrate had cooled to room temperature, a crystal was precipitated. When the crystal was recovered by filtration and dried, 370 g of dihydroxydiphenylsulfone having an absorbance of 0.026 and a Hazen color number of 60 was obtained.

EXAMPLE 2

A liquid mixture comprising 129 g of methanol, 310 g of water and 480 g of the mother liquid obtained in Example 1 (the methanol/water weight ratio was 30/70) was mixed with 650 g of crude dihydroxydiphenylsulfone synthesized in Example 1 and the mixture was heated and refluxed to form a homogeneous solution. Then, 13 g of activated carbon having an average pore diameter of 24 Å and 6.5 g of natural hydrotalcite were added to the so-formed solution, and the mixture was heated and refluxed while stirring for 1 hour. When the activated carbon and hydrotalcite were removed by filtration, a light-brown solution was obtained. When the filtrate had cooled to room temperature, a crystal was precipitated. When the crystal was recovered by filtration and dried, 570 g of dihydroxydiphenylsulfone having an absorbance of 0.007 and a Hazen color number of 5 was obtained.

COMPARATIVE EXAMPLE 2

To a mixed solvent comprising 258 g of methanol and 602 g of water (the methanol/water weight ratio was 30/70) was added 700 g of dihydroxydiphenylsulfone synthesized in the same manner as described in Example 1, and the mixture was heated to form a solution. Then, 14 g of activated carbon having an average pore diameter of 39 Å was added to the solution and the mixture was heated, refluxed, and stirred for 1 hour. The activated carbon was removed from the liquid mixture by filtration, and when the filtrate had cooled, a crystal was precipitated. The crystal was recovered by filtration and dried to obtain 550 g of dihydroxydiphenylsulfone having an absorbance of 0.021 and a Hazen color number of 50.

COMPARATIVE EXAMPLE 3

The procedures of Comparative Example 2 were repeated in the same manner except that 7 g of synthetic hydrotalcite was used instead of 14 g of activated carbon, whereby 560 g of dihydroxydiphenylsulfone having an absorbance of 0.214 was obtained.

EXAMPLE 5

A flask having an capacity of 2 was charged with 200 g of methanol, 800 g of water, 700 g of dihydroxydiphenylsulfone synthesized in the same manner as described in Example 1, 21 g of activated carbon having an average pore diameter of 20 Å and 7 g of synthetic hydrotalcite, and the mixture was heated and refluxed for 1 hour. The composition of the mixed solvent was such that the methanol/water weight ratio was 20/80. A light-brown filtrate obtained by removing the activated carbon and hydrotalcite by filtration was cooled to room temperature, and the precipitated crystal was recovered by filtration and dried to obtain 660 g of dihydroxydiphenylsulfone having an absorbance of 0.005 and a Hazen color number of 0.

We claim:

1. A process for the purification of dihydroxydiphenylsulfone, which comprises heating and mixing colored dihydroxydiphenylsulfone obtained by a reaction between phenol and sulfuric acid with activated carbon and a hydrotalcite compound consisting essentially of a hydrate of a composite salt of magnesium carbonate, magnesium hydroxide and aluminum hydroxide, represented by the formula of $mg_6Al_2(OH)_{16}CO_3.4H_2O$ in a mixed solvent comprising methanol and water at a mixing weight ration of from 20/80 to 40/60, removing the activated carbon and hydrotalcite compound by filtration, cooling the filtrate, and separating a precipitated crystal.

2. A process according to claim 1, wherein the average diameter of pores in the activated carbon is 15 to 60 Å.

3. A process according to claim 1, wherein the hydrotalcite compound is used in an amount of 0.1 to 2 parts by weight per 100 by weight of the colored dihydroxydiphenylsulfone.

4. A process according to claim 1, wherein the colored dihydroxydiphenylsulfone is homogeneously dissolved in the methanol/water mixed solvent and the activated carbon and hydrotalcite are added to the solution.

5. A process according to claim 1, wherein methanol, water, the colored dihydroxydiphenylsulfone, the activated carbon and the hydrotalcite are charged in a dissolving tank and the entire mixture is heated and stirred.

6. A process according to claim 1, wherein the activated carbon and hydrotalcite compound is filtered off by using a filter aid of diatomaceous earth.

7. A process according to claim 1, wherein the average diameter of the pores in the activated carbon is 20 to 50 Å.

* * * * *